(12) United States Patent
Dunn et al.

(10) Patent No.: US 7,090,663 B2
(45) Date of Patent: Aug. 15, 2006

(54) HIGH VOLUME LIQUID WASTE COLLECTION AND DISPOSAL SYSTEM

(75) Inventors: James L. Dunn, Topeka, KS (US); Lawrence E. Guerra, Overland Park, KS (US)

(73) Assignee: Dornoch Medical Systems, Inc., Riverside, MO (US)

( * ) Notice: Subject to any disclaimer, the term of this patent is extended or adjusted under 35 U.S.C. 154(b) by 0 days.

(21) Appl. No.: 10/910,494

(22) Filed: Aug. 3, 2004

(65) Prior Publication Data

US 2005/0010179 A1   Jan. 13, 2005

Related U.S. Application Data

(62) Division of application No. 10/090,221, filed on Mar. 4, 2002, now Pat. No. 6,893,425.

(51) Int. Cl.
*A61M 1/00* (2006.01)
*B08B 3/00* (2006.01)

(52) U.S. Cl. .................. 604/319; 604/323; 604/540; 134/56 R

(58) Field of Classification Search ........ 604/317–327, 604/540–544, 35, 313, 315; 134/56 R, 116, 134/140, 22.18
See application file for complete search history.

(56) References Cited

U.S. PATENT DOCUMENTS

| 3,780,757 | A | * | 12/1973 | Jordan | 137/205 |
|---|---|---|---|---|---|
| 4,384,580 | A | * | 5/1983 | Leviton | 604/320 |
| 4,863,446 | A | * | 9/1989 | Parker | 604/317 |
| 4,863,921 | A | * | 9/1989 | Youssefyeh et al. | 514/230.5 |
| 4,957,491 | A | * | 9/1990 | Parker | 604/319 |
| 5,019,056 | A | * | 5/1991 | Lee et al. | 604/257 |
| 5,242,434 | A | * | 9/1993 | Terry | 604/317 |
| 5,252,340 | A | * | 10/1993 | Honeycutt | 424/489 |
| 5,588,167 | A | * | 12/1996 | Pahno et al. | 5/606 |
| 5,741,238 | A | * | 4/1998 | Bradbury et al. | 604/322 |
| 5,776,118 | A | * | 7/1998 | Seifert et al. | 604/317 |
| 5,885,240 | A | * | 3/1999 | Bradbury et al. | 604/4.01 |
| 5,901,717 | A | * | 5/1999 | Dunn et al. | 134/56 R |
| 5,914,047 | A | * | 6/1999 | Griffiths | 210/739 |
| 5,975,096 | A | * | 11/1999 | Dunn et al. | 134/56 R |
| 5,997,733 | A | * | 12/1999 | Wilbur et al. | 210/85 |
| 6,039,724 | A | * | 3/2000 | Seifert et al. | 604/533 |
| 6,180,000 | B1 | * | 1/2001 | Wilbur et al. | 210/85 |
| 6,263,887 | B1 | * | 7/2001 | Dunn | 134/22.18 |
| 6,588,436 | B1 | * | 7/2003 | Dunn et al. | 134/22.18 |
| 6,695,823 | B1 | * | 2/2004 | Lina et al. | 604/304 |
| 6,776,175 | B1 | * | 8/2004 | Dunn et al. | 134/140 |
| 6,796,317 | B1 | * | 9/2004 | Dunn et al. | 134/116 |
| 6,893,425 | B1 | * | 5/2005 | Dunn et al. | 604/319 |

* cited by examiner

*Primary Examiner*—Tatyana Zalukaeva
*Assistant Examiner*—Michael G. Bogart
(74) *Attorney, Agent, or Firm*—DLA Piper Rudnick Gray Cary US LLP

(57) ABSTRACT

A system for collecting and disposing of liquid medical waste includes a fluid collection cart and a draining and cleaning station. The fluid collection cart includes a pair of containers, each of which includes a draining port and a cap. Liquid level detectors also communicate with each container. The cart also includes a regulator so a low vacuum level may be pulled on one of the containers while a full vacuum level is pulled on the other container. Fluids are collected in the containers via suction tubes connected to the patient ports. The flushing and drain ports of the containers are connected to corresponding flushing and drain connectors on the station when the containers are full so that they may be drained and flushed. The cart liquid level detectors communicate with the station microprocessor so that the draining and flushing cycles may be properly sequenced.

8 Claims, 8 Drawing Sheets

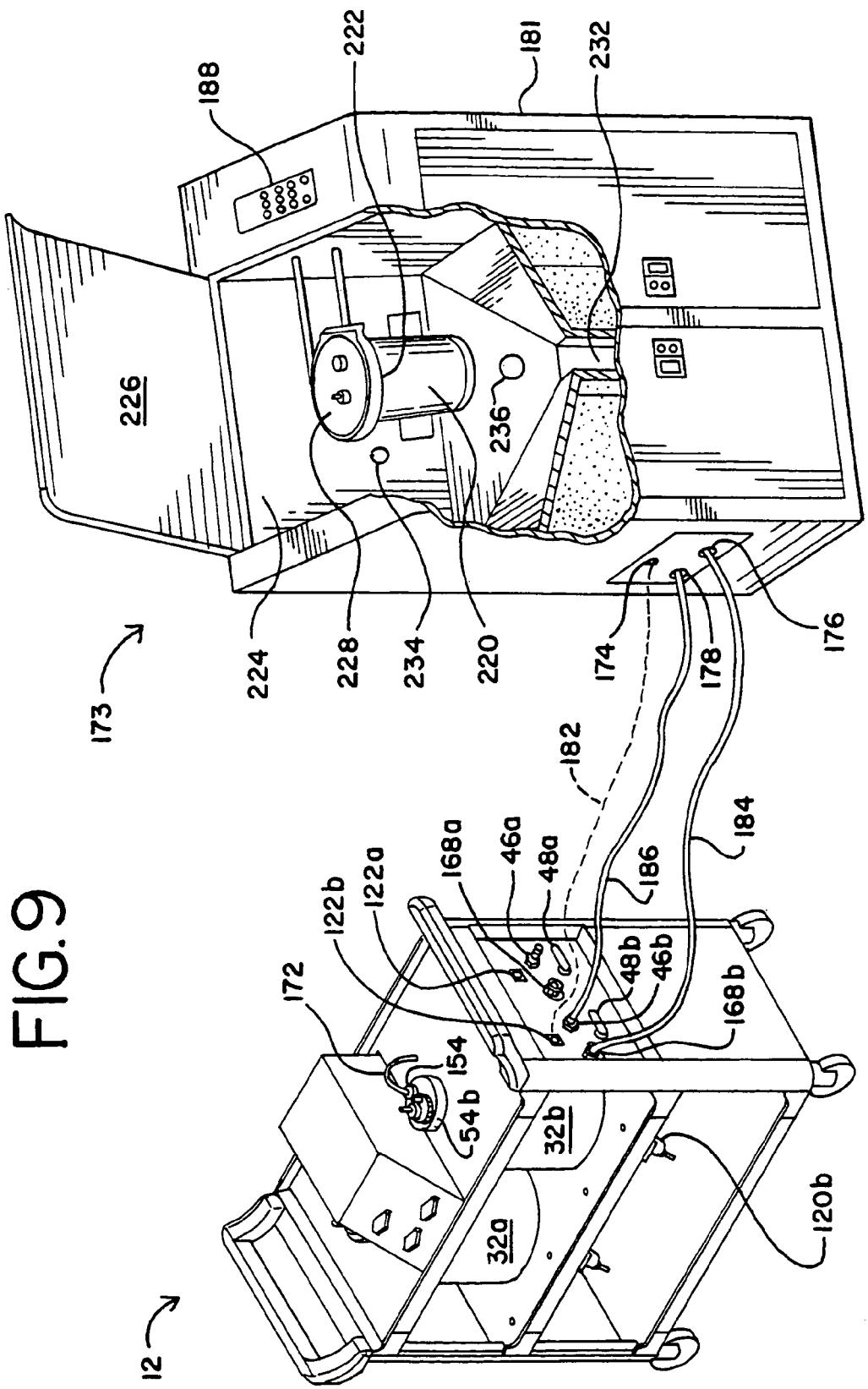

HIGH VOLUME LIQUID WASTE COLLECTION AND DISPOSAL SYSTEM

CROSS-REFERENCE TO RELATED APPLICATION

This application is a division of application Ser. No. 10/090,221, filed Mar. 4, 2002 now U.S. Pat. No 6,893,425.

BACKGROUND OF THE INVENTION

I. Field of the Invention

The present invention relates generally to systems for handling biological fluids and, in particular, to a system for collecting a large volume of liquid waste during a medical procedure and safely disposing of the waste.

II. Description of the Related Art

Various forms of liquid medical wastes are commonly produced in surgery and other medical procedures. Such wastes may include blood and other body fluids of patients. The wastes may also include solid particles such as fragments of bone or cartilage. Some procedures produce a high volume of such waste from a single patient. For example, saline solution is used to irrigate the knee area during arthroscopic procedures. As another example, saline solution is used to flush the bladder, urethra and/or prostate in some urology procedures. Such procedures may produce as much as 30,000 cc of liquid medical waste.

Liquid medical waste generates significant disposal problems due to its possible contamination with various infectious diseases, including AIDS, hepatitis and MRSA. As a result, rules and regulations for the handling and disposal of liquid medical waste have been imposed by various governmental and regulatory agencies. For example, new regulations require the use of engineering controls to protect employees from exposure. In addition, hospitals and other health care facilities have been searching for methods and systems that reduce hospital personnel's exposure to the fluids during collection, handling and disposal. Procedures that produce large volumes of liquid medical waste amplify these issues and concerns.

Various systems and methods have been used for collecting, handling and disposing of fluids from procedures that produce large volumes of liquid medical waste. The collection vessels vary from simple buckets to automated, electronically controlled processing equipment.

A bucket, referred to as a "gravity bucket", may be placed by an operating room table or placed in another convenient location within the room in which a medical procedure is being performed. Flexible tubing typically connects the gravity bucket with the region of the patient from which the fluid wastes are collected. When the gravity bucket becomes filled, it is carried out of the operating room and its contents are poured down a drain. Such an arrangement has several drawbacks. Carrying the open bucket and emptying it manually creates the opportunity for direct human contact with the potentially infected wastes if the fluid spills or leaks from the bucket. In addition, the fluids may splash back or otherwise result in the formation of aerosols that contact the person disposing of the waste.

Suction canisters are commonly used to aspirate fluids from patients during surgical procedures. Such canisters range in volume from around 1200 cc to around 3000 cc. A suction canister typically features a removable lid with a vacuum port and a patient or suction port. During a surgical procedure, the vacuum port is connected by flexible tubing to a hospital vacuum source while the suction port is connected by a second flexible tube to the region of the patient from which the fluid wastes are collected.

As an alternative to a gravity bucket, a number of suction canisters may be positioned on a stand and connected in tandem. The stand features a base positioned on rollers so that the stand may be rolled to, from and around an operating room. A vertical rod extends upwards from the base and has a number of horizontal rings connected thereto. Each ring is sized to hold a suction canister and the rings are positioned on the vertical rod in a spaced and staggered fashion. The eight (for example) canisters positioned on the stand are connected in a tandem fashion as follows. The first canister has its suction port connected to the patient's surgery site by a flexible tube. The vacuum port of the first canister is connected to the suction port of a neighboring second canister. The vacuum port of the second canister is connected to the suction port of a third canister. The arrangement is repeated for the fourth through seventh canisters. The eighth canister suction port is connected to the vacuum port of the seventh canister while the vacuum port of the eighth canister is connected to the hospital vacuum source. As a result, each of the eight canisters is subjected to suction so that fluids produced by the medical procedure are collected in the canisters.

While such an arrangement allows a large volume of fluid to be collected, as the above description reveals, the connection of the canisters is complicated. If one mistake is made in connecting the tubing, no suction is available for the procedure. In addition, the stand becomes somewhat top heavy with the canisters filled so that the cart becomes difficult to maneuver and great care must be exercised when moving the cart. The arrangement also results in a large number of canisters to clean or dispose of as infectious waste. Using the above example, one procedure would result in eight canisters that need to be dumped and cleaned. This is very time consuming. The large number of canisters required also makes the arrangement expensive.

Systems for collecting and disposing of high volumes of fluids are offered by the Steris Corporation of Mentor, Ohio, as the "SafeCycle 40", and Stryker Instruments of Kalamazoo, Michigan, as the "Neptune Waste Management System."

The Steris "SafeCycle 40" system, described in U.S. Pat. Nos. 4,863,446 and 4,957,491, both to Parker, is a fluid collection and disposal system featuring a mobile fluid collection cart and a disposal station. The fluid collection cart includes vacuum and suction ports that communicate with a reservoir that is positioned on the cart. The reservoir also features a drain outlet. A vacuum line connects the vacuum port of the collection cart to a hospital vacuum source during surgery so that fluid is withdrawn from the patient via flexible tubing that is connected to the cart's suction port and collected in the reservoir. The collection cart features a vacuum regulator that permits the level of suction provided by the cart suction ports to be adjusted by knobs on the cart. After surgery, the collection cart is connected to the disposal station via washing and draining connectors so that the reservoir is drained and flushed via a timed cleaning process.

The Stryker "Neptune" system, described in U.S. Pat. Nos. 5,997,733 and 6,180,000, both to Wilbur et al., is a portable waste disposal system that includes a waste collection system, a smoke extraction system and a treatment and disposal system that heats the waste to sanitize it for disposal. The system includes a container that features a vacuum port that is connected to a vacuum source of a hospital. The container also includes a suction port that is in communication with the patient surgery site via flexible tubing. As a result, fluids from the patient are collected in the container. Smoke is withdrawn from the patient surgery site by an additional flexible tube that is in communication with the head space of the container. The smoke is filtered as it is withdrawn from the head space into a housing that contains additional filters and a fan that pulls the smoke into the housing. The container also includes a drain which may either be connected to the treatment system or a hospital drain so that the fluid in the container may be drained or treated and then drained.

While the Steris and Stryker systems have proven to be effective, the systems are unable to accommodate suction canisters of the 1200 cc to 3000 cc variety. As a result, a separate cleaning and disposal system for the smaller suction canisters must be purchased by a hospital in addition to the Steris and Stryker machines. This results in an increase in purchase expenses and personnel training for a hospital or other health care facility. The requirement for two separate systems also results in increased maintenance costs. Due to their complexity, the Steris and Stryker systems are also quite costly. Also due to their complexity, at least in part, the carts of the Steris and Stryker systems are heavy when their containers are full. This makes pushing and maneuvering the carts burdensome.

Accordingly, it is an object of the present invention to provide a system for safely and conveniently collecting a large volume of liquid waste during a medical procedure.

It is another object of the present invention to provide a system that permits large volumes of liquid medical waste to be handled and disposed of without contact by personnel.

It is another object of the present invention to provide a system that simultaneously provides both high and low or gravity drain suction.

It is another object of the present invention to provide a system for collecting, handling and disposing of large volumes of liquid medical waste that is economical to purchase and maintain.

It is still another object of the present invention to provide a system for collecting, handling and disposing of large volumes of liquid medical waste that is easy to configure and operate.

It is still another object of the present invention to provide a system that facilitates handling of large volumes of liquid medical waste.

It is still another object of the present invention to provide a system that accommodates both large volume containers and smaller, individual suction canisters.

It is still another object of the present invention to provide a system for collecting, handling and disposing of large volumes of liquid medical waste that may also withdraw smoke from a patient's surgical site.

Other objects and advantages will be apparent from the remaining portion of this specification.

SUMMARY OF THE INVENTION

A system for collecting and disposing of liquid medical waste includes a cart for collecting medical waste and a station for draining and cleaning the containers of the cart. The cart includes a body supported by a plurality of wheels. First and second containers are mounted on the cart body and each has a drain port and cap positioned thereon. Each cap includes an inner portion and an outer portion. The inner cap portion has a patient port and a vacuum port formed therein. The outer cap portion has a bore formed therein within which the inner cap portion is removably received. A flushing port is also formed in the outer cap portion. A cleaning nozzle is positioned within the container and is in communication with the flushing port. Filters, including possibly an optional smoke plume filter, communicate with each container vacuum port. Liquid level detectors also communicate with the containers.

The cart also includes a vacuum regulator positioned thereon. The regulator selectively communicates with the vacuum port of one of the containers and a hospital vacuum source so that a low vacuum level may be pulled on the container. The vacuum port of the other container bypasses the regulator so that a full vacuum level is simultaneously pulled on the unregulated container. A housing defining a chamber within which the vacuum regulator is positioned features a control panel with valve handles so that the vacuums pulled by the containers may be controlled. Suction lines are attached to the patient ports of the containers so that liquid medical waste is drawn into each container as the vacuums are pulled thereon.

Flushing connectors are in communication with the flushing ports of the containers, drain connectors are in communication with the drain ports of the containers and electrical connectors are in communication with the liquid level detectors. The flushing, drain and electrical connectors are mounted on a side panel of the cart for connection to corresponding connectors on the draining and cleaning station after the cart containers have been filled during a medical procedure. When connected to the draining and cleaning station, the cart containers are drained and flushed. The collected medical waste in the containers may be detected via the liquid level detectors by the station microprocessor when the liquid level detector is placed in communication with the station through the electrical connectors. As a result, the microprocessor can control the sequencing of the container draining and flushing cycles. The draining and cleaning station may also be used to clean suction canisters.

The following detailed description of embodiments of the invention, taken in conjunction with the appended claims and accompanying drawings, provide a more complete understanding of the nature and scope of the invention.

BRIEF DESCRIPTION OF THE DRAWINGS

FIG. 9 is a partially broken-away perspective view of the cart of FIG. 1 connected to a draining and cleaning station;

DETAILED DESCRIPTION OF THE INVENTION

Figure 1:
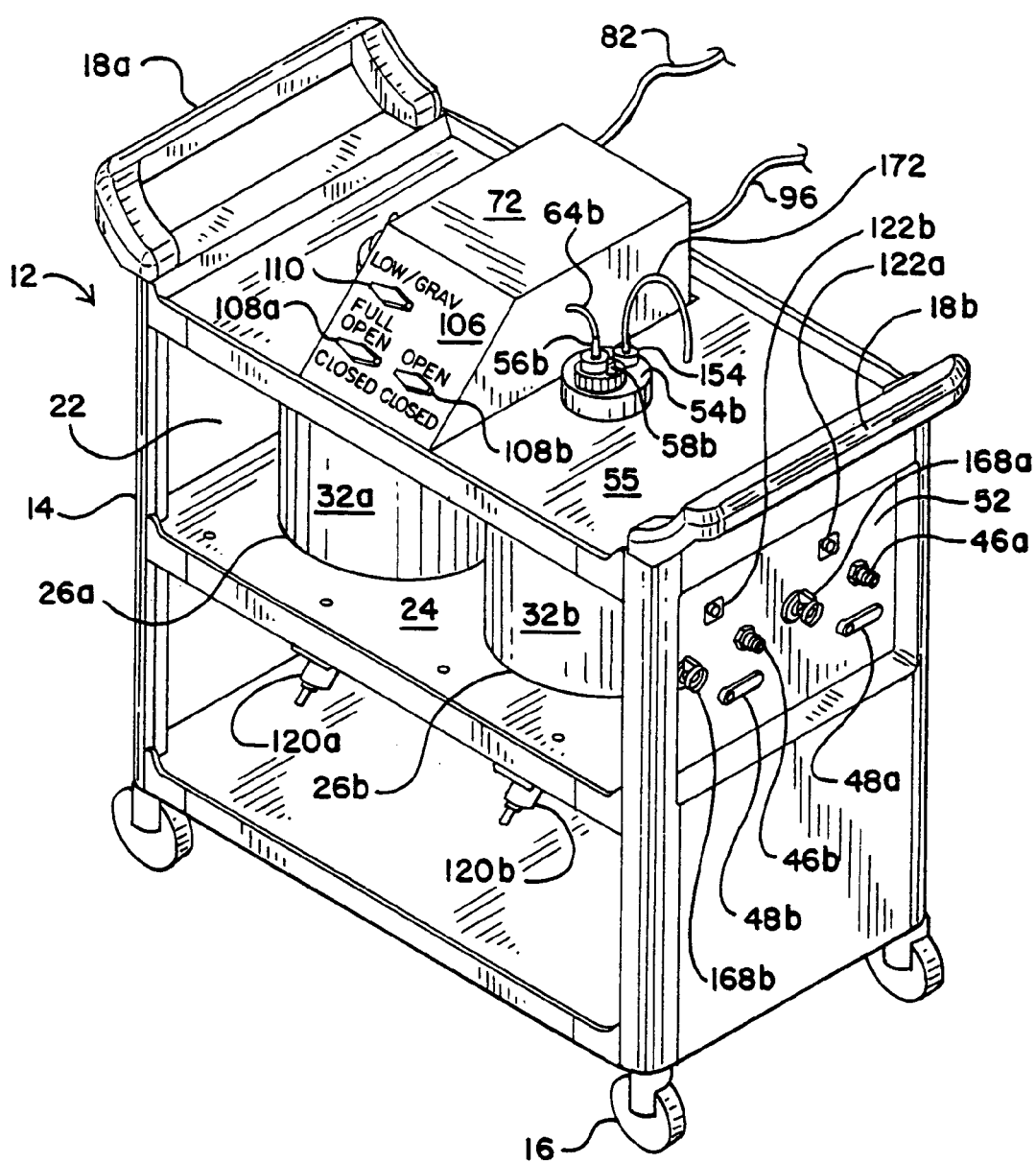
FIG. 1 is a perspective view of a fluid collection cart of an embodiment of the system of the present invention.
Figure 3:
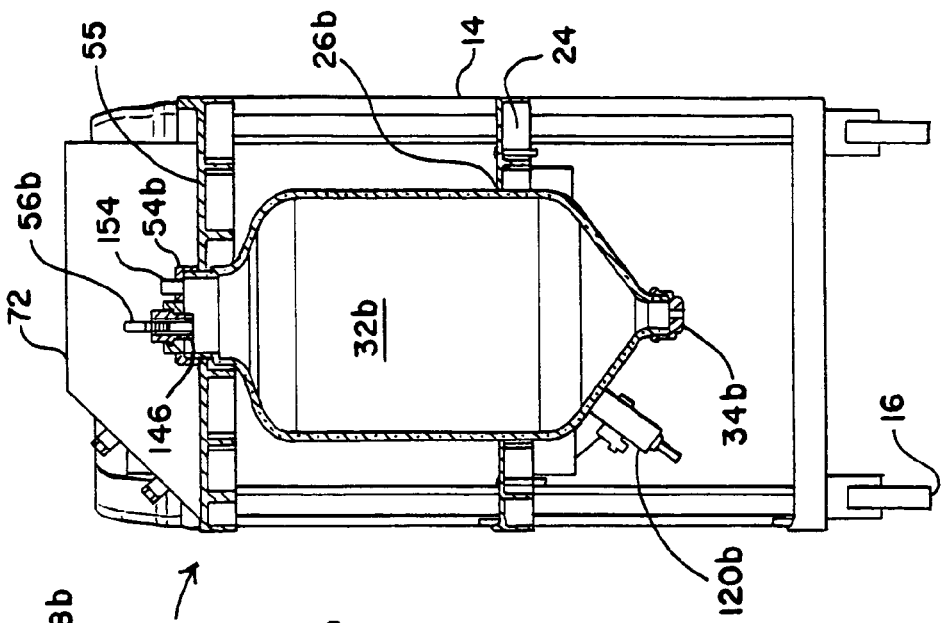
FIG. 3 is a sectional view of the cart of FIG. 2 taken along line 3—3.
Figure 2:
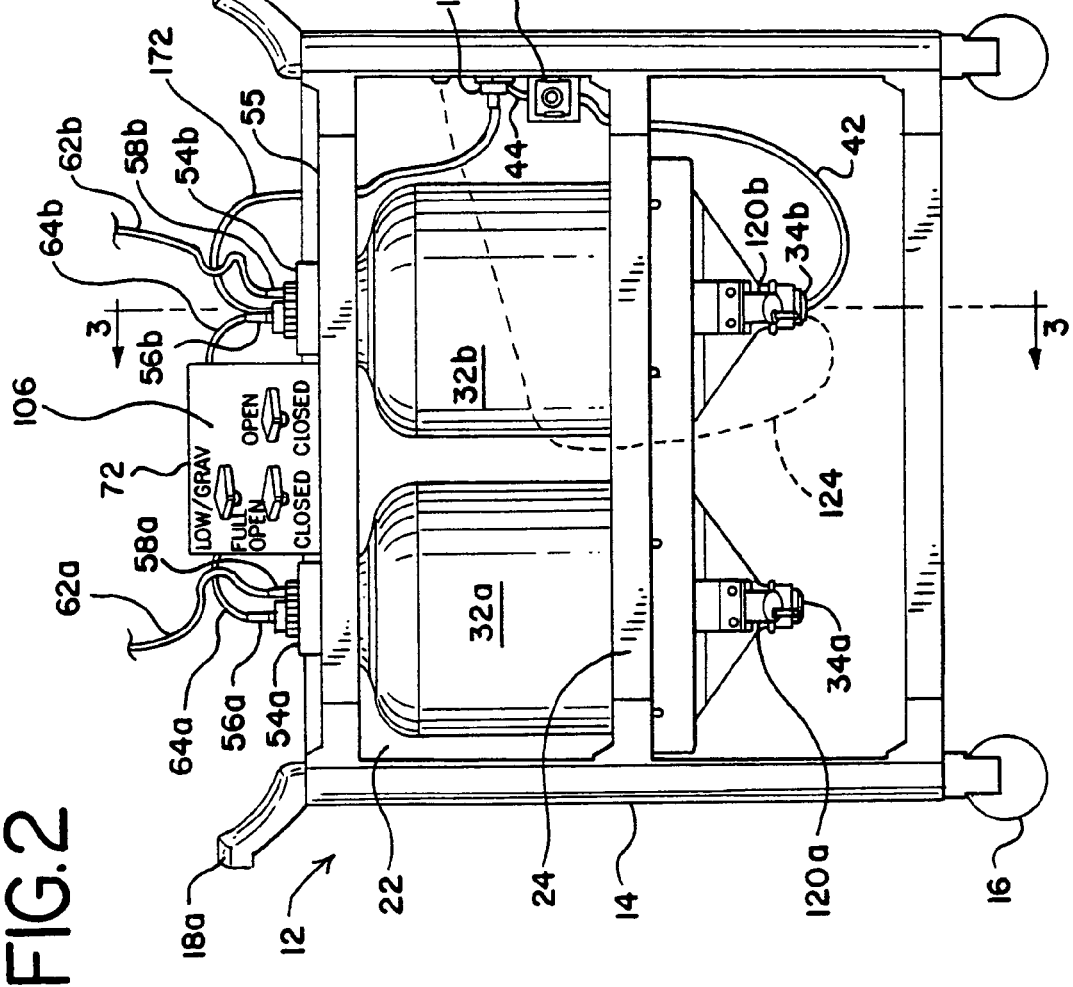
FIG. 2 is a side elevation view of the cart of FIG. 1.

The fluid collection cart of a preferred embodiment of the system of the present invention is indicated in general at 12 in FIGS. 1–3. The cart features a cabinet-like body 14 that is supported at its bottom four corners by wheels 16. Opposing handles 18a and 18b are secured to the top of the cart body 14 to facilitate pushing, pulling and maneuvering of the cart. The cart 12 is preferably constructed of plastic for strength, durability and light weight.

The cart body 14 defines an interior space 22 within which a shelf 24 is mounted. While not illustrated, doors may optionally be provided on the cart so that the interior space 22 is hidden from view when the doors are closed. Shelf 24 features a pair of openings 26a and 26b formed therein within which bottle-shaped containers 32a and 32b are secured. Containers 32a and 32b are preferably constructed of glass for ease of cleaning and are sized to hold approximately six gallons of liquid each.

As illustrated in FIGS. 2 and 3, the bottom of each container 32a and 32b is provided with a drain port, 34a and 34b, respectively. As illustrated in FIG. 2, drain port 34b is connected to the inlet of a drain valve 36 by line 42. The outlet of drain valve 36 communicates by line 44 with a drain connector, illustrated at 46b in FIG. 1. Both drain valve 36 and drain connector 46b are mounted to a side panel 52 of cart 12. Drain valve 36 may be opened or closed by drain valve handle 48b. When drain valve 36 is closed, communication between the drain connector 46b and the drain port 34b of container 32b is prevented. When drain valve 36 is open, fluid within container 32b flows to drain connector 46b. Drain connector 46a is connected to drain port 34a of container 32a in a similar fashion through a valve (not shown) that is controlled by drain valve handle 48a. The associated tubing has been omitted from FIG. 2 for the sake of clarity. In addition, all tubing has been omitted from FIG. 3 for the sake of clarity. Drain valve handles 48a and 48b are configured so that their corresponding valves are closed when the cart is used during a medical procedure to collect biological fluids.

Figure 8:
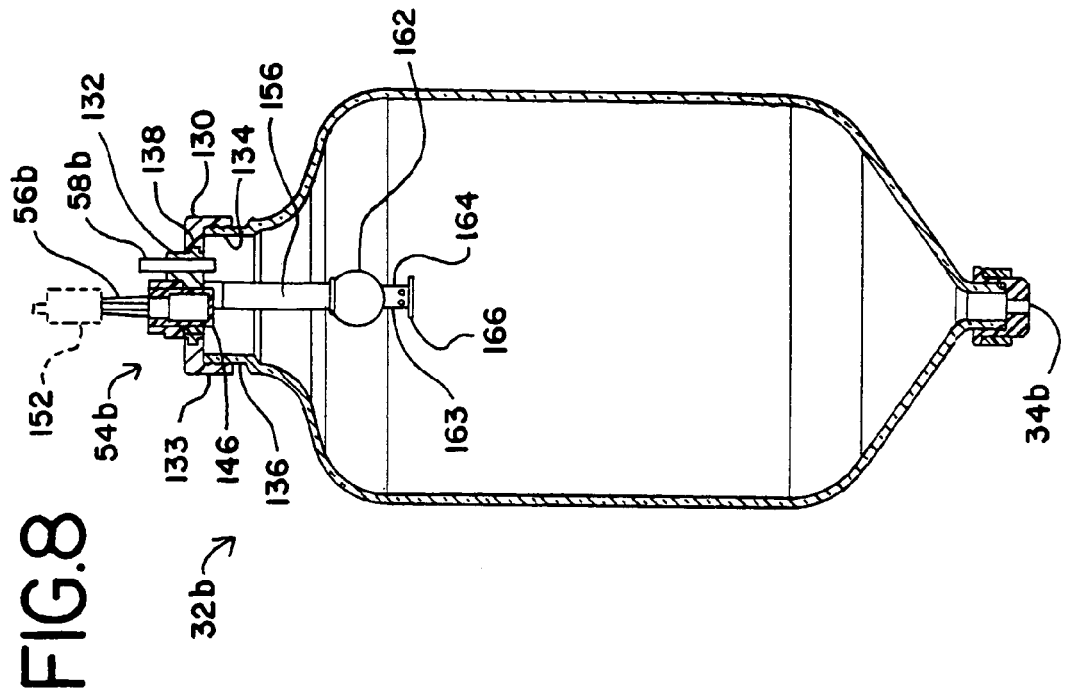
FIG. 8 is a sectional view of the container of FIG. 7 taken along line 8—8.

The tops of containers 32a and 32b are closed by caps 54a and 54b, respectively, which extend through the top surface 55 of cart body 14. Caps 54a and 54b preferably are constructed of plastic and feature vacuum ports 56a and 56b and patient or suction ports 58a and 58b. As illustrated in FIG. 2, the suction ports 58a and 58b are connected to flexible tubing suction lines 62a and 62b which lead to the region of the patient from which the fluid wastes are collected. Fluids are withdrawn from the patent via tubing 62a and 62b and collected in containers 32a and 32b, respectively, when vacuums are pulled on the containers via vacuum ports 56a and 56b. Vacuum ports 56a and 56b are connected via flexible tubing 64a and 64b, respectively, to a regulator housing 72 that is mounted upon the top surface 55 of the cart body 14. As illustrated in FIG. 8, the vacuum port is equipped with a Porex filter 146 that, in addition to filtering (as will be described below), may cooperate with the hospital vacuum source to automatically stop suction when the canister is full.

Figure 4:
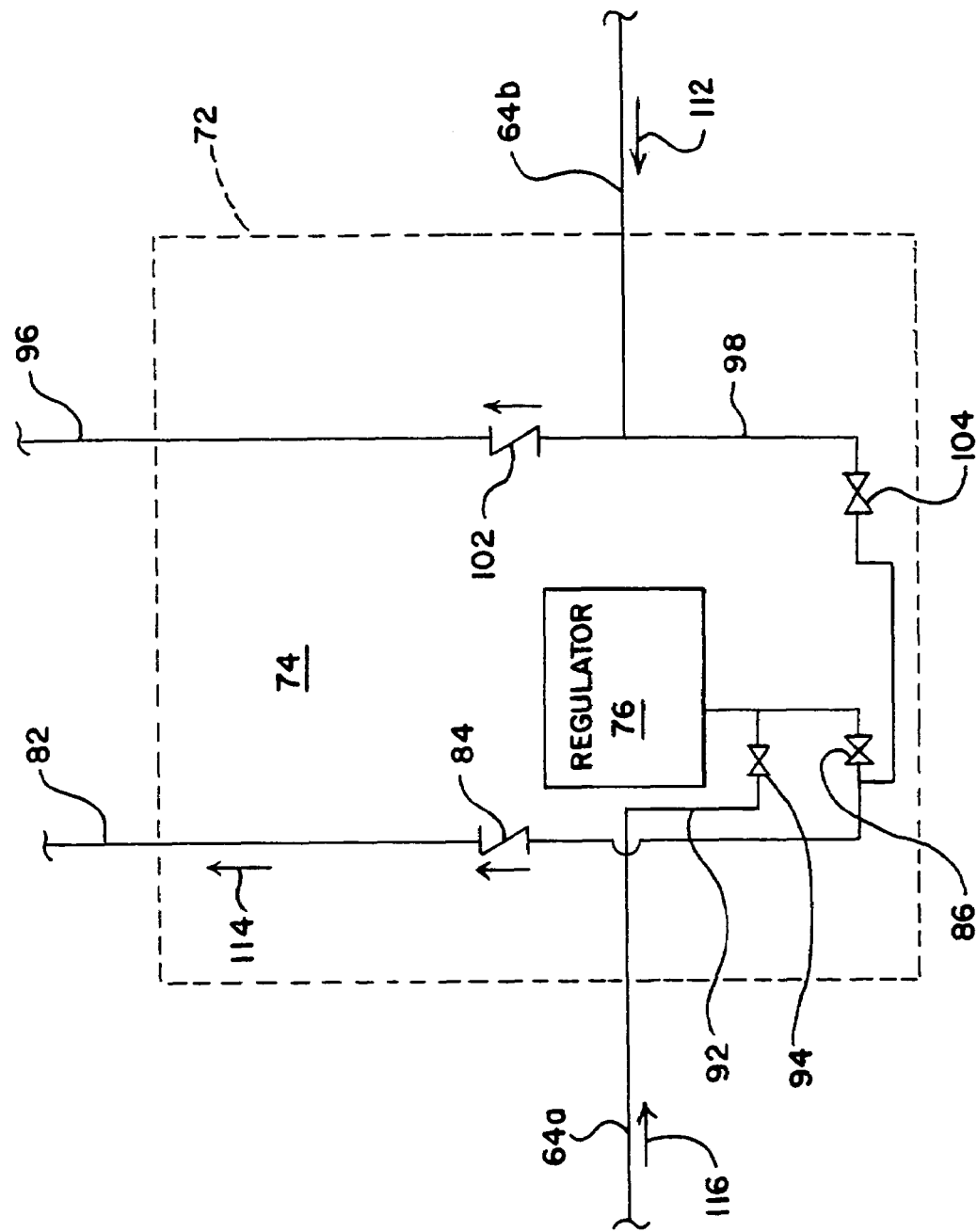
FIG. 4 is a schematic view of the regulator housing of the cart of FIGS. 1–3.

As illustrated in FIG. 4, housing 72 defines a chamber 74 that features a regulator 76 preferably set to 5 in. Hg and associated valves and piping. More specifically, line 64a leads to regulator 76. A vacuum source line 82 is connected to a hospital vacuum source and communicates with regulator 76 through check valve 84 and control valve 86. A bypass line 92 connects line 82 with line 64a through bypass valve 94. A second vacuum source line 96 may be placed in communication with a second hospital vacuum source and communicates with line 64b and crossover line 98 through check valve 102. Crossover line 98 is equipped with control valve 104 and communicates with hospital vacuum source line 82.

As illustrated in FIG. 1, housing 72 features a control panel 106 featuring valve handles 108a, 108b and 110. All three valve handles may be manipulated between two positions. Valve handles 108a and 108b may both be toggled between "open" and "closed" settings. Valve handle 110 may be toggled between "full" and "low/gravity drain" settings. Valve handle 108a configures control valve 86 of FIG. 4 between the open and closed positions, valve handle 108b configures control valve 104 of FIG. 4 between the open and closed positions and valve handle 110 configures control valve 94 of FIG. 4. The "full" setting of valve handle 110 corresponds to an open condition for bypass valve 94 and a "low/gravity drain" setting of valve handle 110 corresponds to a closed condition for bypass valve 94.

The operating mode of the cart during a medical procedure depends upon the configuration of valve handles 108a, 108b and 110 and whether one or both of vacuum source lines 82 and 96 are connected to hospital vacuum sources. Taking first the situation where only vacuum source line 82 is connected to a hospital vacuum source, a full vacuum of approximately 25 in. Hg is pulled on container 32b through lines 64b, 98 and 82, as illustrated by arrows 112 and 114, when valve 104 is opened (via valve handle 108b of FIG. 1).

With the cart connected to a single hospital vacuum source through line 82, and a full vacuum being pulled on container 32b, container 32a may simultaneously pull a low or gravity drain vacuum of approximately 5 in. Hg when valve handle 108a (FIG. 1) is placed in the "open" position, so that valve 86 is open, and valve handle 110 is placed in the "low/gravity drain" position so that bypass valve 94 is closed. With reference to FIG. 4, this results in a vacuum being pulled on line 64a, as illustrated by arrow 116, and thus container 32a, by line 82 through regulator 76 so that the vacuum pulled on line 64a and container 32a is limited by regulator 76 to 5 in. Hg. As a result, the system of the present invention provides for both high level suction and gravity drain via suction lines 62b and 62a (FIG. 2), simultaneously during a medical procedure.

If valve 104 is shut, by placing corresponding valve handle 108b of FIG. 1 in the "closed" position, no vacuum is pulled on container 32b and either a low vacuum of approximately 5 in. Hg or a high vacuum of approximately 25 in. Hg may be pulled on container 32a by toggling valve handle 110 between the "low/gravity drain" and "full" positions, respectively. With valve handle 110 set to the "full" position, bypass valve 94 is opened so that the vacuum pulled on line 64a, and thus canister 32a, by line 82 bypasses regulator 76. Of course, valve 86 must be open, with corresponding valve handle 108a of FIG. 1 placed in the "open" position.

If both lines 82 and 96 are connected to hospital vacuum sources, and valves 86, 104 and 94 are open, a full vacuum of approximately 25 in. Hg is pulled on each container 32a and 32b.

As illustrated at 120a and 120b in FIGS. 1–3, a liquid level detector is positioned on the bottom of each container 32a and 32b. While other devices known in the art may be used, liquid level detectors 120a and 120b preferably are capacitance sensors. As illustrated in FIG. 2, capacitance sensor 120b is connected to electrical connector 122b, shown mounted to the cart body side panel 52 in FIG. 1, by electrical line 124. Sensor 120a is connected to electrical connector 122a of FIG. 1 in a similar fashion, however, the corresponding electrical line has been omitted from FIG. 2 for the sake of clarity. As will be explained below, the sensors 120a and 120b and electrical connectors 122a and 122b, along with drain connectors 46a and 46b, find use during the draining and flushing or cleaning cycles.

Figure 6:
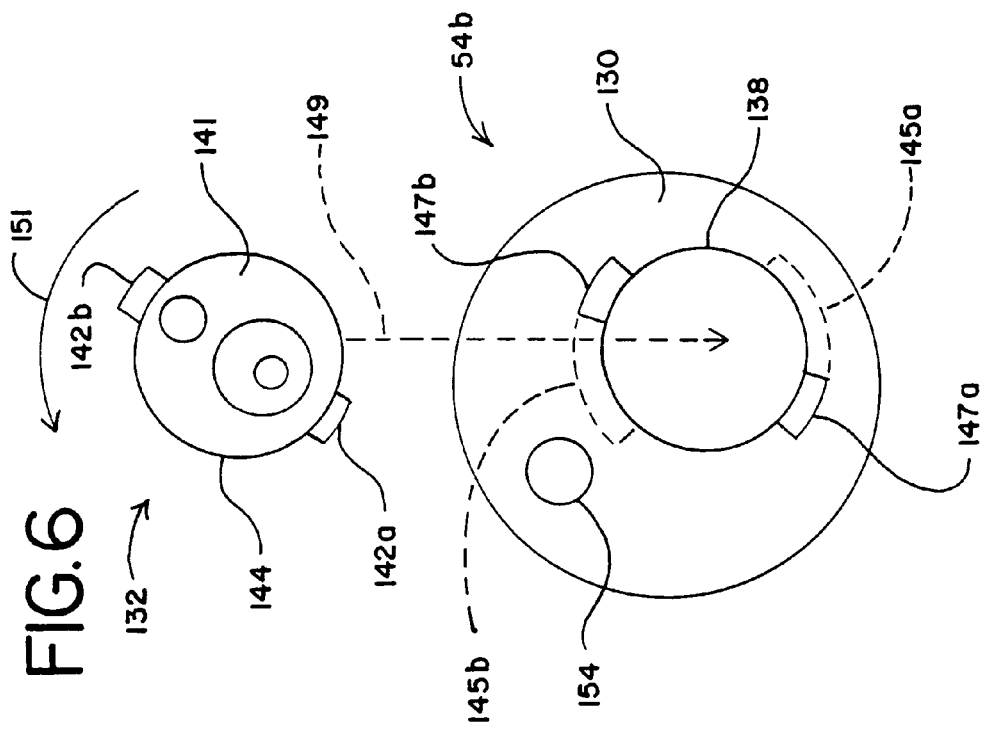
FIG. 6 is an exploded top plan view of the container cap of FIG. 5.
Figure 5:
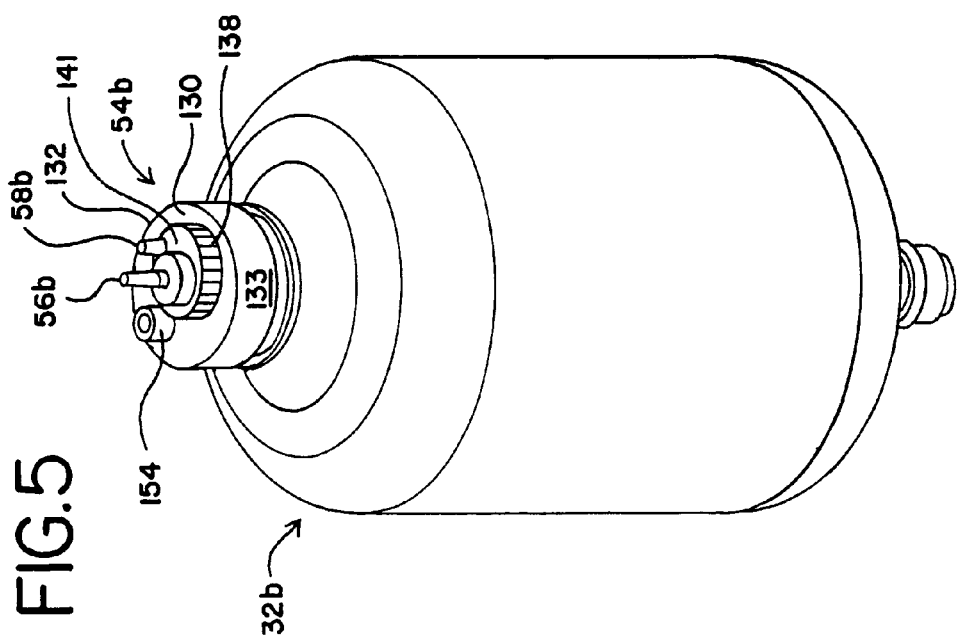
FIG. 5 is an enlarged perspective view of one of the containers of the cart of FIGS. 1–3.
Figure 7:
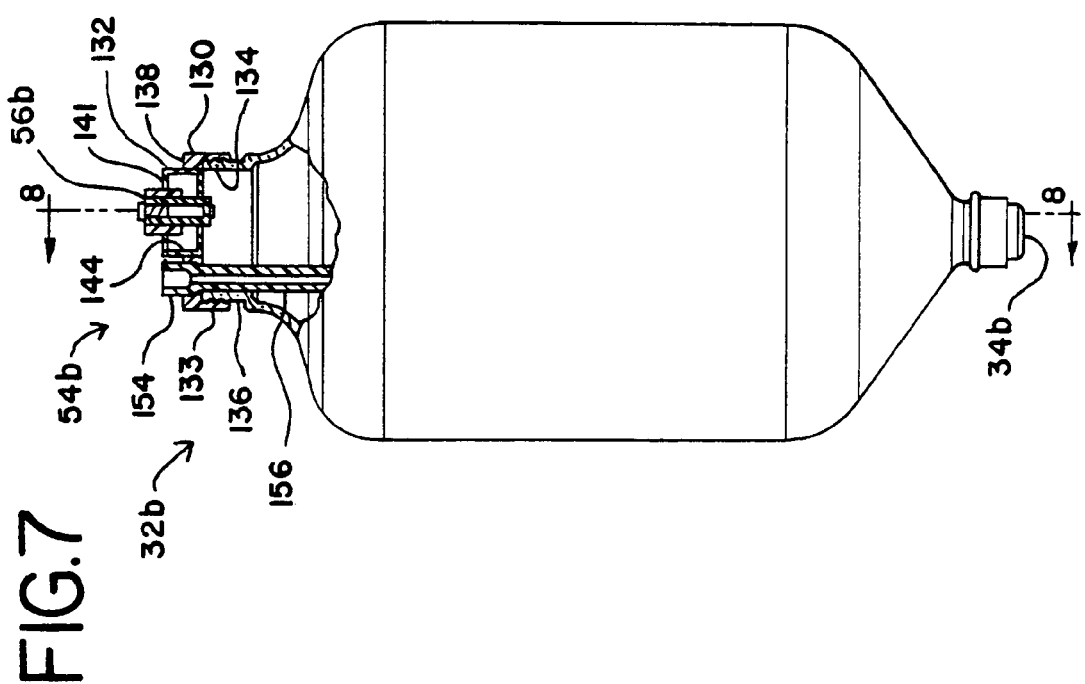
FIG. 7 is a partially broken-away side elevation view of the container of FIG. 5.

Enlarged and detailed views of container 32b are presented in FIGS. 5, 7 and 8. It is to be understood that container 32a features an identical construction. As illustrated in FIGS. 5–8, plastic cap 54b includes an outer portion 130 and an inner portion 132. As illustrated in FIGS. 7 and 8, the outer portion 130 of cap 54b features a downward extending skirt 133 with a threaded inner surface 134. The outer cap portion 130 screws onto the threaded top opening 136 of container 32b via threaded inner surface 134 and also features a bore 138.

The inner portion 132 of cap 54b features vacuum port 56b and patient or suction port 58b formed in its circular surface 141. In addition, as illustrated in FIG. 6, inner cap portion 132 has a pair of opposing tabs 142a and 142b formed on its circumference 144. Corresponding horizontal slots 145a and 145b are formed in the bore 138 of outer cap portion 130. A pair of vertical channels 147a and 147b corresponding to the width of the tabs are formed between the top surface of the outer cap portion 130 and the horizontal slots 145a and 145b. As a result, as indicated by dashed arrow 149 in FIG. 6, the tabs 142a and 142b of the inner cap portion 132 may be lowered via the vertical channels 147a and 147b into the horizontal slots 145a and 145b and turned in the direction indicated by arrow 151 so that the inner cap portion 132 is locked within the bore 138 of the outer cap portion 130.

As a result, inner cap portion 132 may be removed from the outer cap portion 130 for disposal after use. This is desirable in that potentially contaminated biological fluids from a medical procedure flow through suction port 58b during a medical procedure. In addition, as illustrated in FIG. 8, the vacuum port 56b is provided with a Porex filter 146. This prevents bacteria and fluids from entering the hospital vacuum source. It is thus desirable to dispose of the Porex filter after use. This is also accomplished by disposing of the inner cap portion 132.

It should be noted that other temporary inner cap portion fastening arrangements may be substituted for the one illustrated in FIG. 6. For example, bore 138 of outer cap portion 130 and the circumference 144 of inner cap portion 132 could be provided with mating threads so that the inner cap portion is screwed into the bore of the outer cap portion.

During a surgical procedure, the surgical site of a patient may undergo procedures that produce smoke. Examples of such procedures include cauterizing and drilling. Such smoke contains foul smelling and potentially infectious airborne particles. As a result, for sanitary reasons, such smoke must removed from the patient's surgical site. As illustrated in phantom at 152 in FIG. 8, a smoke plume filter may optionally be connected to vacuum port 56b so as to be in series with line 64b of FIGS. 1 and 2. Such filters are known in the art and permit the canister 32b to collect smoke from a patient's surgery site via suction tube 62b of FIG. 2. In order to accomplish this, full suction (approximately 25 in. Hg) must be pulled on canister 32b.

As illustrated in FIGS. 5–7, the outer cap portion 130 is equipped with a flushing port 154. As illustrated in FIG. 7, the flushing port 154 communicates with a conduit 156, preferably constructed of plastic, that extends down into the interior of container 32b. Positioned on the end of conduit 156 is a cleaning nozzle, illustrated at 162 in FIG. 8. Cleaning nozzle 162 preferably rotates when liquid is supplied thereto so that water and cleaning solution flowing to the nozzle is sprayed onto the interior surfaces of container 32b.

In some instances, the spray provided by nozzle 162 causes the pressure within container 32b to increase rapidly. The increased pressure within the container 32b causes liquid to back up in conduit 156, sometimes as high as six to eight inches. To combat this occurrence, a "top hat" shaped piece 163 may optionally be added to conduit 156 so as to extend below the nozzle 162. The top hat piece features a number of orifices 164 through which liquid from the conduit flows. The liquid then cascades over the brim 166 of the top hat piece. As a result, the pressure head within the container 32b is collapsed so that the back up of liquid into conduit 156 does not occur.

With reference to FIGS. 1 and 2, the flushing port 154 is connected to a flushing connector 168b via flexible tubing 172. The flushing port of the cap of container 32a is connected to the flushing connector 168a of FIG. 1 in a similar fashion. Both flushing connectors 168a and 168b are mounted to the side panel 52 of cart body 14. As with electrical connectors 122a and 122b and drain connectors 46a and 46b, the flushing connectors 168a and 168b find use during the draining and cleaning cycles which now will be described. The flushing connectors 168a and 168b feature integral valves that seal when the connectors are not connected to lines so that vacuums may be pulled within containers 32a and 32b during fluid collection.

After a medical procedure is completed, or the containers 32a and 32b are filled, lines 82 and 96 (FIG. 1) are disconnected from the hospital vacuum source(s) and suction lines 62a and 62b (FIG. 2) are disconnected from the suction ports 58a and 58b. Caps are then placed upon the suction ports and the cart is wheeled out of the operating room to a separate room containing the draining and cleaning station. As will be described below, a modified version of the "RedAway II" system sold by Dornoch Medical Systems, Inc. of Riverside, Mo. may be used as the draining and cleaning station for the cart. The RedAway II system is described in detail in pending U.S. patent application Ser. No. 09/870,215, the contents of which are incorporated herein by reference.

FIG. 9 illustrates the cart 12 connected to the draining and cleaning station, indicated in general at 173, so that the container 32b of cart 12 may be drained and cleaned. Similar to cart 12, draining and cleaning station 173 features electrical, flushing and drain connectors, illustrated at 174, 176 and 178, respectively. As illustrated in FIG. 9, the electrical, flushing and drain connectors of the cart, 122b, 168b and 46b, are each connected to the corresponding connectors positioned on the housing 181 of cleaning station 173 by line 182 and flexible tubing 184 and 186, respectively. After these connections are made, drain valve handle 48b is opened. The entire draining and cleaning process may now be controlled from the control panel 188 of the station 173.

Figure 10:
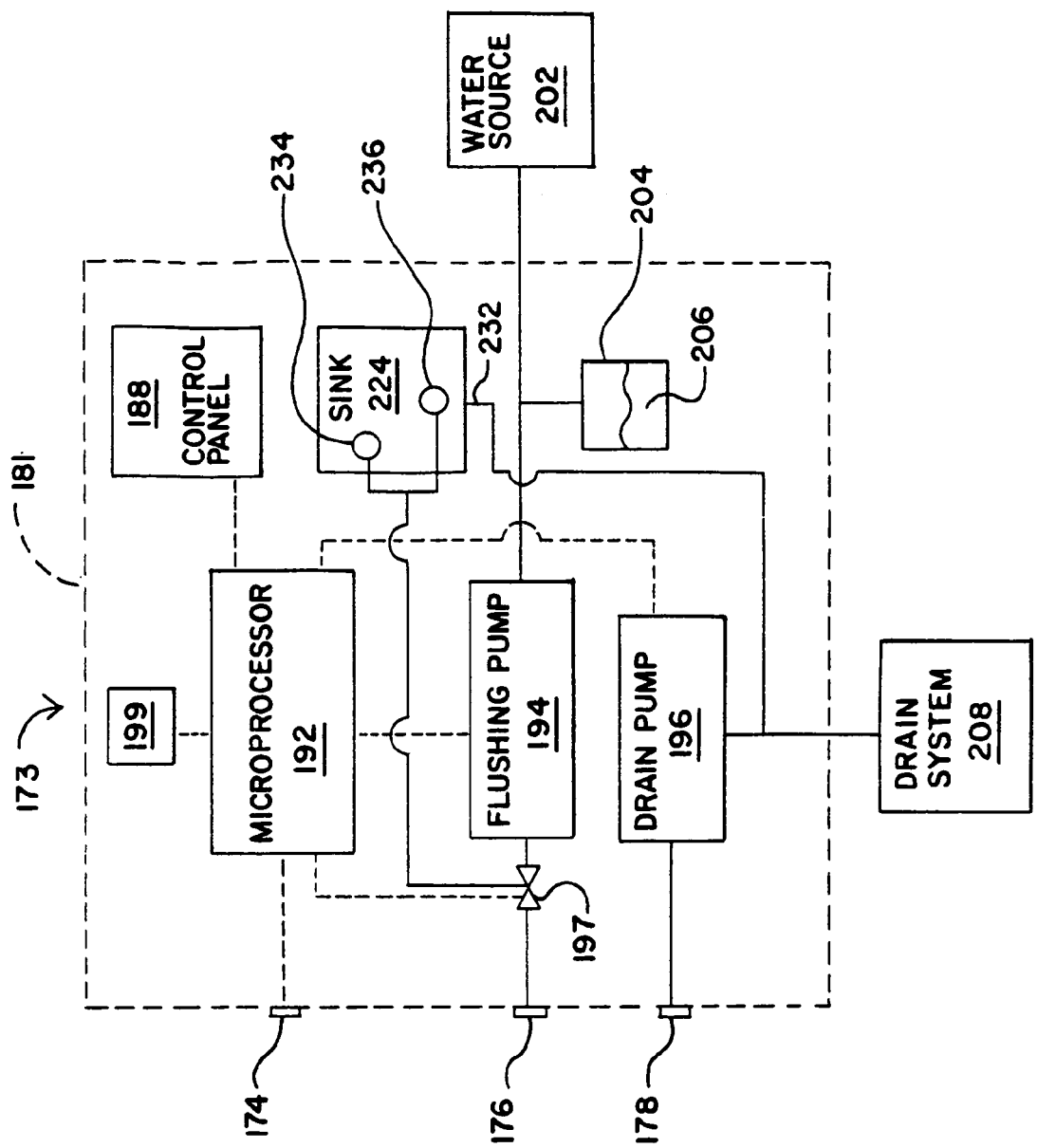
FIG. 10 is a schematic view of the draining and cleaning station of FIG. 9.

As illustrated in FIG. 10, the draining and cleaning station 173 includes a microprocessor 192 that communicates with capacitance sensor 120b via electrical connectors 174, 122b, line 182 and line 124 (FIG. 2). The microprocessor also communicates with the control panel 188 of the cleaning station as well as a drain pump 194 and a flushing pump 196. The flushing pump inlet is in communication with a water supply source 202. A dispenser 204 containing a supply of bleach 206, or other additive, is positioned within the draining and cleaning station cabinet 181 and also communicates with the water supply source 202 and the inlet of flushing pump 194. The drain pump communicates with the hospital or health care facility drainage system 208. The drain and flushing pumps 196 and 194 also communicate with the drain and flushing connectors 178 and 176.

Microprocessor 192 also communicates with an automated control valve 197. Control valve 197 may be configured to route the mixture of bleach and water from pump 194 to either flushing connector 176 or spray jets 234 and 236, which are positioned in the sink 224 of the station. The microprocessor also communicates with the draining and cleaning station canister handling mechanism 199. As will be explained below, these components permit the draining and cleaning station to drain and flush suction canisters and are disabled when the station is draining and flushing the containers of cart 12.

Figure 11:
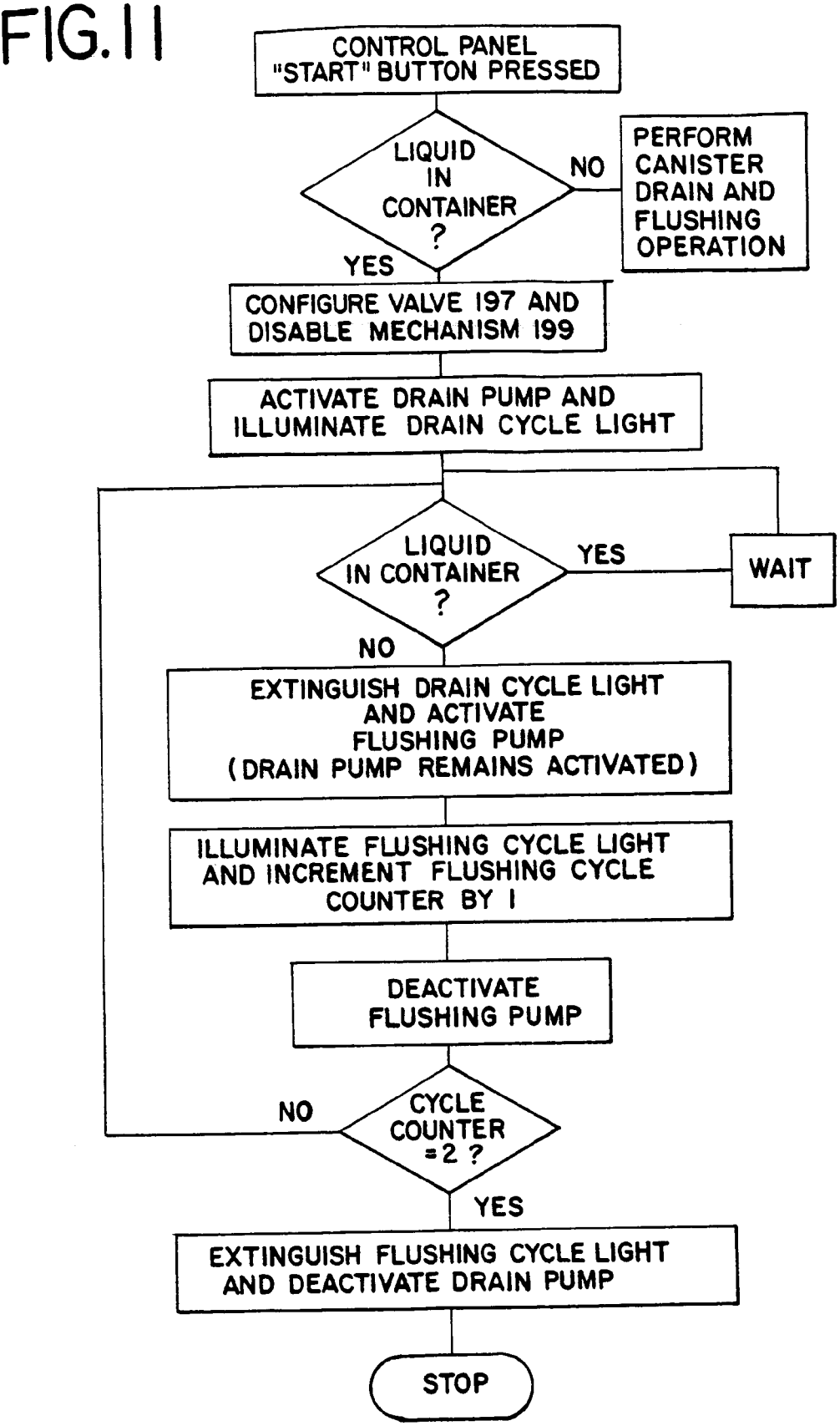
FIG. 11 is a flow diagram showing the steps of the software program of the microprocessor of FIG. 10.

The processing performed by the microprocessor 192 of FIG. 10 is illustrated in FIG. 11. When the draining cycle is initiated by a "start" button on control panel 188, the microprocessor first checks for the presence of liquid waste in container 32b via capacitance sensor 120b (FIGS. 1–3). If liquid waste is in container 32b, as will be discussed in greater detail below, the microprocessor reconfigures valve 197 and disables canister handling mechanism 199. The microprocessor also illuminates a "drain cycle" indicator light on the control panel 188 and activates drain pump 196 so that the contents of the container are drained through line 42 (FIG. 2), line 186 (FIG. 9) and directed to the drain system 208.

When the capacitance sensor 120b (FIGS. 1–3) indicates to the microprocessor that the liquid waste has been drained from the container, flushing pump 194 is activated. The "drain cycle" indicator light on panel 188 is also extinguished and a "flushing cycle" indicator light is illuminated. Flushing pump 194 sends a stream consisting of a mixture of water and bleach, from water source 202 and dispenser 204, respectively, through lines 184 and 172 (FIG. 9) to the flushing port 154 of the cap 54b of container 32b. As a result, the interior of container 32b is sprayed with the water and bleach mixture by the nozzle 162 of FIG. 8. Drain pump 196 remains activated so that the mixture of bleach, water and residue is withdrawn from the container and directed to drain system 208.

After a period of time, the flushing pump is deactivated. The drain pump continues to run so that all of the liquid in container 32b drains. When the capacitance sensor 120b indicates that the container is empty, the flushing pump is once again activated so that the flushing cycle is repeated. Microprocessor 192 keeps track of the number of flushing cycles performed by using, for example, the cycle counter included in FIG. 11. Preferably, two or three flushing cycles are performed. When the last flushing cycle is performed, the "flushing cycle" light on control panel 188 is extinguished and the drain pump is deactivated. The draining and flushing cycles are then completed. Container 32b is then prepared for reuse by the removal and disposal of the inner cap portion 132 (FIGS. 5–8). A new replacement inner cap portion 132 is then installed.

Once draining and flushing of container 32b is completed, the drain valve handle 48b is closed and the connectors 174, 176 and 178 of station 173 are disconnected from connectors 122b, 168b and 46b. The station connectors are then reconnected to cart connectors 122a, 168a and 46a and drain valve handle 48a is opened so that container 32a may be drained and flushed.

As described in U.S. application No. 09/870,215, when cart 12 is not present, the draining and cleaning station may alternatively be used to clean suction canisters. With reference to FIG. 9, a filled canister 220 is placed within a bracket 222 which is secured within sink 224 which is positioned within the housing 181 of the station. After the lid 226 of the station is closed, and the "start" button on control panel 188 is pressed, the lid 228 of the canister is automatically removed and the canister is rotated about a horizontal axis by the canister handling mechanism (199 in FIG. 10). The contents of the canister then drain into the sink 224 and down drains 232 and 208 (FIGS. 9 and 10). Spray jets 234 and 236 then spray the inverted canister with a mixture of bleach and water (FIGS. 9 and 10). As illustrated in FIG. 11, when the capacitance sensor of cart 12 is connected to the draining and cleaning station 173, and the station "start" button is pressed, the microprocessor of the station recognizes the presence a filled cart container and reconfigures valve 197 of FIG. 10 so that liquid from the pump is directed to connector 176 and the canister handling mechanism 199 is also disabled so that the canister cleaning operation cannot be performed.

While FIGS. 9–11 are described with respect to the draining and cleaning machine of U.S. patent application Ser. No. 09/870,215, other canister draining and cleaning stations or systems may be easily modified to clean the containers of cart 12. These stations include those illustrated in U.S. Pat. Nos. 6,263,887 and 5,901,717, the latter of which is sold by Dornoch Medical Systems, Inc. as the "RedAway I" system. Both patents are also owned by Dornoch Medical Systems, Inc.

While the preferred embodiments of the invention have been shown and described, it will be apparent to those skilled in the art that changes and modifications may be made therein without departing from the spirit of the invention, the scope of which is defined by the appended claims.

What is claimed is:

1. A system for collecting and disposing of liquid waste comprising:
   a) a fluid collection cart including:
      i) a body supported by a plurality of wheels;
      ii) a container supported by said body and featuring vacuum, patient, flushing and drain ports, where liquid waste is collected within the container through the patient port when the vacuum port is connected to a vacuum source and the flushing and drain ports are closed;
   b) a station including;
      i) a cabinet having a sink with an open top and drain and flushing connectors, said sink and said drain connector in communication with a drain and said flushing connector adapted to communicate with a water source;
      ii) a canister that is separate and distinct from the container of the cart and that features a removable lid;
      iii) means for securing the canister filled with liquid waste within the sink;
      iv) means for draining the liquid waste from the canister into the sink and drain;
      v) means for flushing residue out of the canister, said means for flushing adapted to communicate with the water source; whereby the drain and flushing connectors of the station may be connected to the drain and flushing ports of the cart container so that liquid waste collected within the container may be drained through the drain of the station and flushed with water from the water source.

2. The system for collecting and disposing of liquid waste of claim 1 further comprising a liquid level sensor in communication with the container of said fluid collection cart and microprocessor positioned within the cabinet of said station, said microprocessor selectively communicating with said liquid level sensor so that the microprocessor may sequence the draining and flushing of the cart container.

3. The system of claim 2 wherein said liquid level detector is a capacitance sensor.

4. The system of claim 2 further comprising a flushing connector in communication with said flushing port, a drain connector in communication with said drain port and an electrical connector in communication with said liquid level detector, said flushing, drain and electrical connectors mounted upon a side panel of said cart.

5. The system of claim 1 further comprising a vacuum regulator positioned on the body of said cart and in communication with said vacuum port of said container, said vacuum regulator adapted to selectively communicate with the vacuum source so that a vacuum level pulled on the container may be regulated.

6. The system of claim 5:
wherein said container is a first container, and
further comprising a second container supported by said body and having a cap that includes vacuum and patient ports, said patient port adapted to selectively communicate with a suction line and said vacuum port adapted to selectively communicate with the vacuum source so that an unregulated, full vacuum level may be pulled on the second container while a regulated vacuum level is simultaneously pulled on the first container.

7. The system of claim 6 wherein said cap includes an inner portion and an outer portion, said inner cap portion having said patient port and said vacuum port formed therein and said outer cap portion having said flushing port and a bore formed therein with said inner cap portion removably received within the bore of said outer cap portion.

8. The system of claim 7 further comprising a cleaning nozzle positioned within said container and in communication with said flushing port.

* * * * *